(12) United States Patent
Kurokawa et al.

(10) Patent No.: US 6,848,294 B2
(45) Date of Patent: Feb. 1, 2005

(54) METHOD AND APPARATUS FOR MONITORING OXYGEN CONCENTRATION IN A BEVERAGE PRODUCTION PROCESS

(75) Inventors: Daisaku Kurokawa, Yaizu (JP); Satoshi Sekibata, Natori (JP); Mitsushiro Saito, Natori (JP); Rikiya Goto, Shibuya-ku (JP)

(73) Assignee: Sapporo Breweries Ltd., Tokyo (JP)

( * ) Notice: Subject to any disclaimer, the term of this patent is extended or adjusted under 35 U.S.C. 154(b) by 0 days.

(21) Appl. No.: 10/724,159

(22) Filed: Dec. 1, 2003

(65) Prior Publication Data
US 2004/0107763 A1 Jun. 10, 2004

Related U.S. Application Data

(62) Division of application No. 10/148,198, filed as application No. PCT/JP01/09289 on Oct. 23, 2001, now Pat. No. 6,679,097.

(30) Foreign Application Priority Data

Oct. 25, 2000 (JP) .................................... 2000-326126

(51) Int. Cl.[7] .................................................. G01N 7/00
(52) U.S. Cl. ........................................ 73/19.01; 702/24
(58) Field of Search .............................. 73/19.01, 19.05, 73/19.06, 19.1; 702/24

(56) References Cited

U.S. PATENT DOCUMENTS

| | | | |
|---|---|---|---|
| 3,740,320 A | | 6/1973 | Arthur |
| 3,849,070 A | | 11/1974 | Garza et al. |
| 4,120,192 A | * | 10/1978 | Williamson ................ 73/19.1 |
| 4,129,029 A | | 12/1978 | Moll et al. |
| 4,282,182 A | | 8/1981 | Webster |
| 4,550,590 A | * | 11/1985 | Kesson ..................... 73/19.05 |
| 4,579,631 A | * | 4/1986 | Ishikawa et al. ......... 205/782.5 |
| 4,926,681 A | * | 5/1990 | Fitzpatrick .................... 73/52 |
| 5,426,593 A | | 6/1995 | Seiden et al. |
| 5,604,297 A | | 2/1997 | Seiden et al. |
| 5,911,910 A | | 6/1999 | Becraft et al. |
| 6,003,362 A | * | 12/1999 | Dieckmann et al. ....... 73/19.12 |
| 6,032,438 A | | 3/2000 | Sanfilippo et al. |
| 6,192,737 B1 | * | 2/2001 | Ohlrogge et al. ......... 73/19.06 |
| 6,228,259 B1 | | 5/2001 | Schwartz et al. |
| 6,395,538 B1 | * | 5/2002 | Naughton et al. ....... 435/288.7 |
| 2003/0029228 A1 | * | 2/2003 | Bloder et al. ............. 73/53.01 |

FOREIGN PATENT DOCUMENTS

| | | |
|---|---|---|
| JP | 58043290 A | 12/1983 |
| JP | 4-315943 | 11/1992 |
| JP | 10-10020 | 1/1998 |

* cited by examiner

*Primary Examiner*—Charles D. Garber
(74) *Attorney, Agent, or Firm*—Oblon, Spivak, McClelland, Maier & Neustadt, P.C.

(57) ABSTRACT

The present invention continuously monitors the amount of oxygen dissolved in a beverage in a beverage storage tank in a beverage filler. Gas is continuously sampled via the vent holes 28 and the vent pipe 29 from the space part inside the beverage storage tank 1 of the beverage filler and is supplied to the oxygen measuring apparatus 40. The oxygen measuring apparatus 40 includes the oxygen measuring device 45 and measures the concentration of oxygen gas of the delivered gas. Based on the concentration of oxygen gas, it is monitored whether or not the amount of oxygen dissolved in the beer inside the storage tank is at or below a predetermined level. Further, the beverage is sampled from a supply channel supplying the beverage to the beverage storage tank so that the concentration of oxygen in the beverage is measured and monitored.

4 Claims, 5 Drawing Sheets

METHOD AND APPARATUS FOR MONITORING OXYGEN CONCENTRATION IN A BEVERAGE PRODUCTION PROCESS

CROSS-REFERENCE TO RELATED APPLICATIONS

This is a divisional application of application Ser. No. 10/148,198, filed Jun. 7, 2000 now U.S. Pat. No. 6,679,097. This application is based upon and claims the benefit of priority from Japanese Patent Application No. 2000-326126, filed Oct. 23, 2000, the entire contents of which are incorporated herein by reference.

TECHNICAL FIELD

The present invention relates to a method of monitoring oxygen concentration in a production process of tea beverages or alcoholic beverages including beer and an apparatus for executing the same.

BACKGROUND ART

The oxidation of tea beverages such as tea and green tea and alcoholic beverages such as beer and sparkling liquor progresses with the passage of time after their production, so that their flavor gradually deteriorates. This is mainly due to oxygen entering these beverages in the process of their production. In the case of beer, for instance, if only an extremely small amount of oxygen enters the beer during its production process, the oxygen molecules are partially reduced by electrons transferred from metal (Fe, Cu) ions existing in the beer in its preserved state so that active oxygen is produced. The active oxygen oxidizes a variety of ingredients in the beer, such as isohumulone and alcohols, and generates aldehydes, which is the cause of aging odor, thereby deteriorating the flavor.

DISCLOSURE OF THE INVENTION

A variety of methods of reducing entry of oxygen in the production process of beverages as much as possible have been studied as one of measures to prevent the oxidation of beverages. In order to achieve this, it is necessary to constantly know the concentration of oxygen in the production process, so that various studies have been conducted of effective timing and method of knowing.

It is an object of the present invention to provide a monitoring method and apparatus for constantly monitoring the concentration of oxygen in real time throughout the production process of beverages. By measuring and monitoring the amount of oxygen dissolved in a beverage immediately before filling and the oxygen concentration of the vapor phase in a storage tank storing the beverage immediately before filling, an overall estimation of the effect of oxygen is made based on both of the concentrations of oxygen.

The inventors of the present invention have focused on the amount of oxygen dissolved in the beverage before filling in the production process and the concentration of oxygen included, immediately before filling, in the vapor phase formed in the storage tank storing the beverage.

The storage tank is internally occupied by the beverage to be filled and the vapor phase of the space part, and the amount of oxygen dissolved in the beverage is affected by the concentration of oxygen in the vapor phase.

That is, in this case, equilibrium is established between the liquid phase taken up by the beverage and the vapor phase of the space part. Therefore, if there is a difference in the concentration of oxygen between the phases, oxygen moves from the phase of high density to the phase of low density to cancel the difference in concentration, so that the concentrations converge into a state of equilibrium. Accordingly, if the concentration of oxygen in the vapor phase of the storage tank is higher than the concentration of oxygen in the beverage, oxygen moves from the vapor phase into the beverage so that the amount of dissolved oxygen is increased.

Normally, replacement is performed in the space part with gas that does not affect the flavor of the beverage, such as carbon dioxide or nitrogen gas. Accordingly, the quality of the gas to be supplied greatly affects the concentration of oxygen in the space part. Entry of oxygen may occur if the gas supply system has a defect or a failure.

Further, in the case of filling a container with the beverage, the container is filled with carbon dioxide or nitrogen gas, and the beverage is filled into the container with the filling gas being discharged. Generally, the discharged filling gas is supplied into the storage tank at this point. In this case, if replacement with the filling gas is not fully performed inside the container due to the malfunction of a filling device, the filling gas having a large amount of oxygen remaining therein is delivered into the storage tank.

Further, even if the concentration of oxygen in the space part inside the storage tank is low, entry of oxygen into the beverage occurring previously at the time of producing the beverage itself may be revealed in the form of an increase in the concentration of oxygen dissolved in the beverage.

Thus, according to the present invention, the concentration of oxygen in the vapor phase part inside the storage tank and the concentration of oxygen dissolved in the beverage inside the storage tank are measured, and the effect of oxygen on the beverage is determined from both concentrations of oxygen.

Further, according to the present invention, the concentration of oxygen in the vapor part in the storage tank and the concentration of oxygen included in the beverage flowing through a supply channel supplying the beverage to the storage tank are measured and monitored, and the effect of oxygen on the beverage is determined from both concentrations of oxygen. Thereby, the concentration of oxygen dissolved into the beverage in the process of producing the beverage itself, which process is upstream from the filling process, and the concentration of oxygen in the space part of the storage tank can be monitored respectively, so that the process responsible for the entry of oxygen can be specified.

Further, as a system for constantly measuring and monitoring the concentration of oxygen in the vapor phase of the space part inside the storage tank in real time, an oxygen sensor may be attached directly to the storage tank to measure the concentration of oxygen in the space part inside the tank, and the measured data (electrical signal) may be displayed on a determination apparatus or a display unit that is separately provided externally. Alternatively, gas in the space part inside the storage tank may be discharged outside, and the concentration of oxygen in the discharged gas may be measured by a measuring device to be determined and displayed. As an oxygen concentration meter employed in this case, a measuring apparatus using a galvanic cell type oxygen sensor, a zirconia type oxygen sensor, or a thermoparamagnetic oxygen sensor may be employed.

Further, as a device for measuring the concentration of oxygen dissolved in the beverage, the above-described oxygen concentration measuring apparatus using a sensor using a galvanic cell type oxygen sensor or a zirconia type oxygen sensor is employed, and the sensor is attached to the storage tank or the pipe channel supplying the beverage to the storage tank.

If it is confirmed, as a result of measuring the concentration of oxygen, that the concentration of oxygen exceeds a given allowable value, the beverage filling operation is stopped based on the measurement information from the measuring apparatus, and a warning is issued. Alternatively, if the measurement reveals that the excess of the concentration of oxygen over the given value is caused, for instance, by the concentration of oxygen in the space part inside the storage tank, the primary cause of the increase in the concentration of oxygen can be improved by increasing the supply of carbon dioxide or nitrogen gas to the storage tank.

A mode of the present invention is a method of monitoring a concentration of oxygen in a beverage production process, the method characterized by including: a step of continuously sampling gas in a space part inside a beverage storage tank storing a beverage to be filled, the beverage storage tank being provided to a beverage filler; a step of measuring a concentration of oxygen in the sampled gas; a step of comparing the measured value and a preset first reference concentration; a first determination step of issuing an alarm signal when the measured concentration of oxygen exceeds the first reference value;

a step of continuously measuring a concentration of oxygen included in the beverage inside the beverage storage tank; a second comparison step of comparing the measured concentration of oxygen in the beverage with a preset second reference value; and a second determination step of issuing an alarm signal when the measured concentration of oxygen in the beverage exceeds the second reference value.

Another mode of the present invention is a method of monitoring a concentration of oxygen in a beverage production process, the method characterized by including: a step of continuously sampling gas in a space part inside a beverage storage tank storing a beverage to be filled, the beverage storage tank being provided to a beverage filler; a step of measuring a concentration of oxygen in the sampled gas; a step of comparing the measured value and a preset first reference concentration; a first determination step of issuing an alarm signal when the measured concentration of oxygen exceeds the first reference value;

a step of continuously measuring a concentration of oxygen included in the beverage flowing through a beverage supply channel supplying the beverage to the beverage storage tank storing the beverage to be filled, the beverage storage tank being provided to the beverage filler; a second comparison step of comparing the measured concentration of oxygen in the beverage with a preset second reference value; and a second determination step of issuing an alarm signal when the measured concentration of oxygen in the beverage exceeds the second reference value.

Yet another mode of the present invention is an apparatus for monitoring a concentration of oxygen in a beverage production process, the apparatus characterized by including: sampling means for continuously sampling gas in a space part inside a beverage storage tank storing a beverage to be filled, the beverage storage tank being provided to a beverage filler; measuring means for measuring a concentration of oxygen in the sampled gas; comparison means for comparing the measured value and a preset first reference concentration; first determination means for issuing an alarm signal when the measured concentration of oxygen exceeds the first reference value;

measuring means for continuously measuring a concentration of oxygen included in the beverage inside the beverage storage tank; comparison means for comparing the measured concentration of oxygen in the beverage with a preset second reference value; and second determination means for issuing an alarm signal when the measured concentration of oxygen in the beverage exceeds the second reference value.

Yet another mode of the present invention is an apparatus for monitoring a concentration of oxygen in a beverage production process, the apparatus characterized by including: sampling means for continuously sampling gas in a space part inside a beverage storage tank storing a beverage to be filled, the beverage storage tank being provided to a beverage filler; measuring means for measuring a concentration of oxygen in the sampled gas; first comparison means for comparing the measured value and a preset first reference concentration; first determination means for issuing an alarm signal when the measured concentration of oxygen exceeds the first reference value;

measuring means for continuously measuring a concentration of oxygen included in the beverage flowing through a beverage supply channel supplying the beverage to the beverage storage tank storing the beverage to be filled, the beverage storage tank being provided to the beverage filler; second comparison means for comparing the measured concentration of oxygen in the beverage with a preset second reference value; and second determination means for issuing an alarm signal when the measured concentration of oxygen in the beverage exceeds the second reference value.

Yet another mode of the present invention is an apparatus for monitoring a concentration of oxygen in a beverage production process, the apparatus characterized by including: a flow channel for gas in a space part inside a beverage storage tank for storing a beverage to be filled to flow through to outside the beverage storage tank, the beverage storage tank being provided to a rotary beverage filler;

a distributor for receiving the gas from the flow channel and delivering the gas outside the beverage filler, the distributor being provided to a rotating central shaft part of the beverage storage tank; an oxygen measuring device constantly measuring a concentration of oxygen in the gas delivered from said distributor; a delivery device for delivering the gas inside the space part to the oxygen concentration measuring device via the flow channel and the distributor; and a determination device comparing the concentration of oxygen from the oxygen concentration measuring device with a preset reference value and issuing an alarm signal when the measured value exceeds the reference value.

In the above-described modes of the present invention, the concentration of oxygen in the vapor phase of the space part inside the beverage storage tank and the concentration of oxygen included in the beverage in the beverage storage tank are constantly monitored, and an alarm signal is issued when the concentrations of oxygen exceed the given reference values. Thereby, the quality of the beverage to be filled can constantly be increased.

Further, in measuring and monitoring the concentration of oxygen in the vapor phase of the space part inside the beverage storage tank, the gas can be sampled continuously from the space part so that the alarm signal may be issued when the given reference value is exceeded.

BEST MODE FOR CARRYING OUT THE INVENTION

A description will now be given of an embodiment in which the present invention is applied to the beer filling process of a production process of beer, referring to the drawings for a further detailed description of the present invention.

Figure 1:
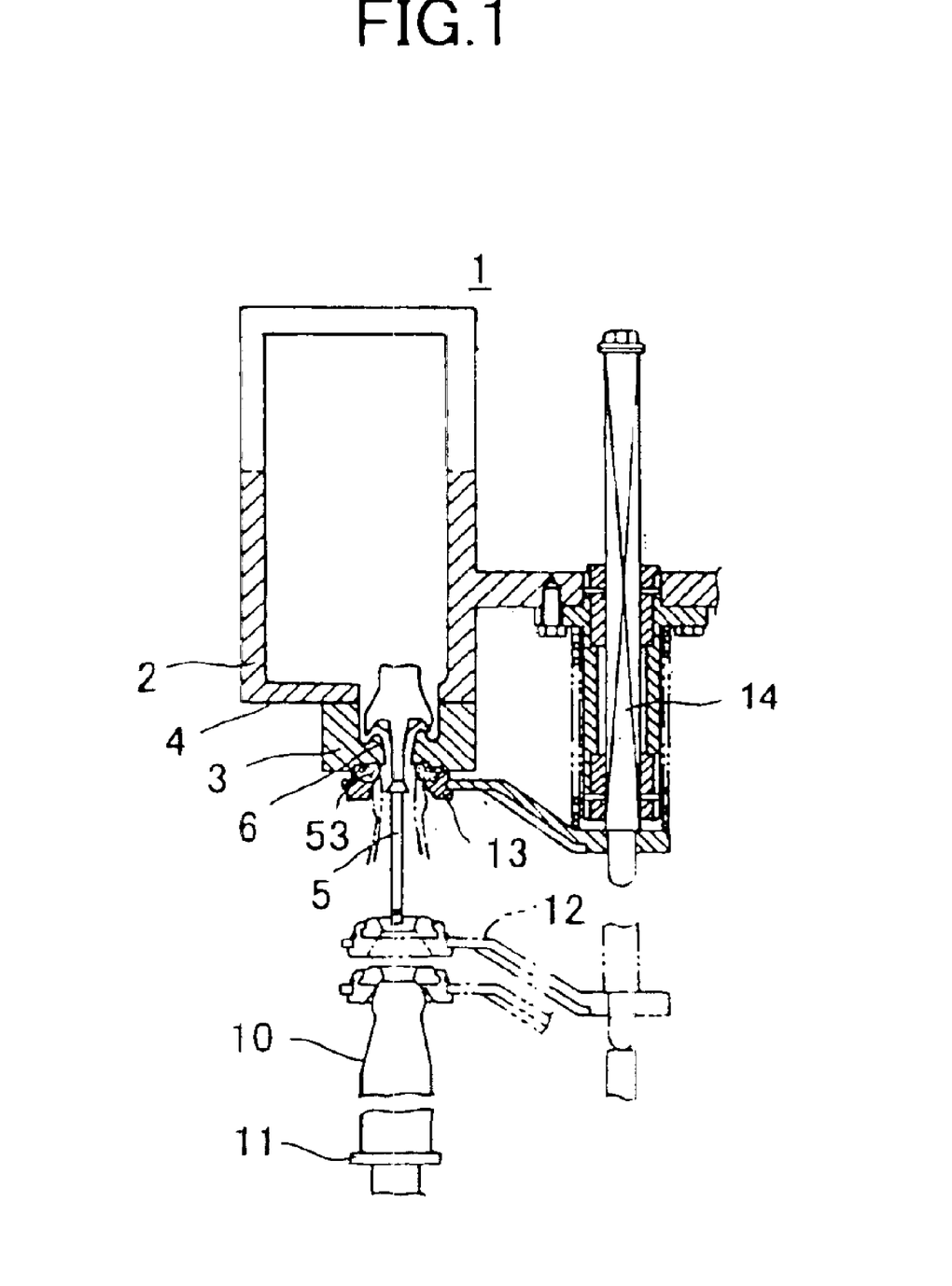
FIG. 1 is a diagram illustrative of a filling mechanism of a beer filler.

FIG. 1 shows a beer filler 1 to which the present invention is applied. The filler 1 includes an annular storage tank (filler bowl) 2. A plurality of filling valves 3 are provided equally spaced on the bottom part of the storage tank 2. The filling valves 3 each include a liquid valve 4 and a vent tube 5. The valve 4 operates so that liquid is injected into a bottle 10 contacting a supply opening 6.

The bottle 10 to be injected with the liquid is transferred to and placed on an elevating stand 11 provided below the storage tank 2. The elevating stand 11 is elevated so that the bottle 10 has its mouth closely contacting the supply opening 6. Reference numeral 12 denotes a support member for positioning the bottle 10 to the supply opening 6. The bottle mount is positioned through a seal member 13. The support member 12 is supported by a sliding bar 14 sliding upward and downward so as to move upward and downward in accordance with the upward and downward movements of the bottle 10. Not shown in the drawing, this embodiment is a rotary beverage filler, and filling of containers is performed with the entire configuration of FIG. 1 being rotated about a rotation axis not shown in the drawing.

Figure 2:
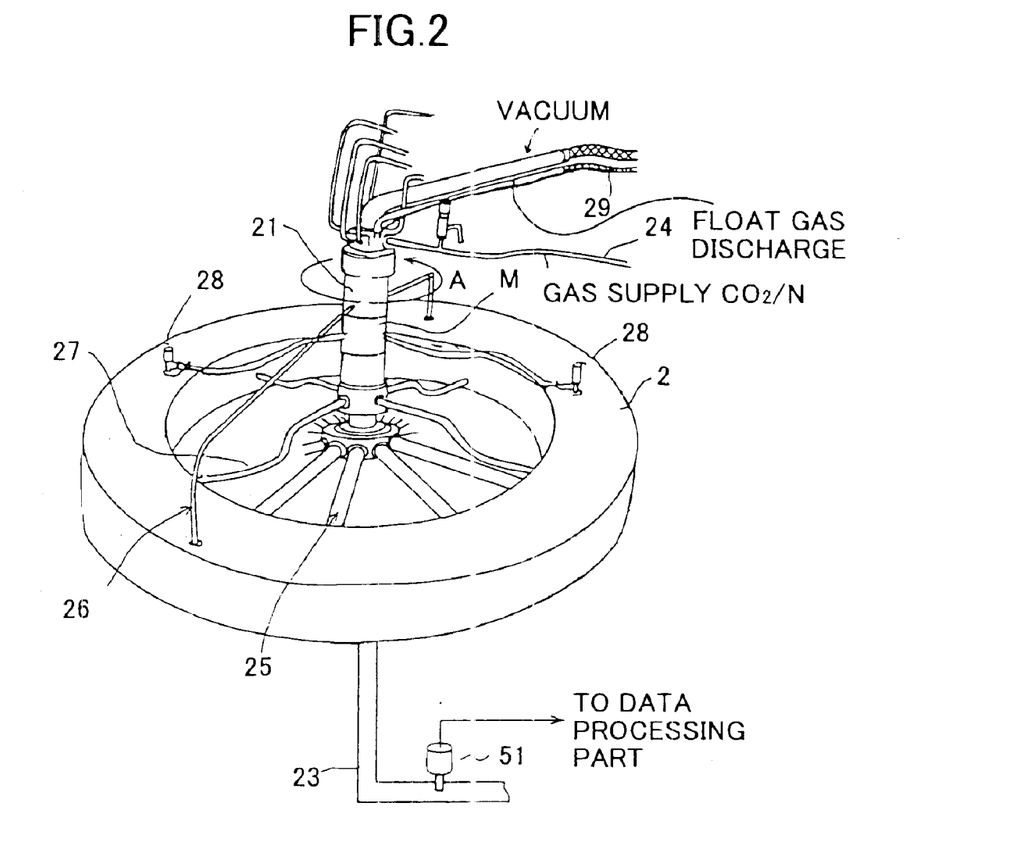
FIG. 2 is a diagram illustrative of a storage tank of the beer filler.

FIG. 2 shows an upper structure of the beer filler 1. Various pipes are connected via a distributor 21 to the upper part of the storage tank 2 and the storage tank 2 so that the beer and gases are supplied thereto or discharged therefrom. As previously described, the beverage filler of this embodiment is a rotary filler, so that the storage tank 2 rotates as well. Not shown in detail in FIG. 2, the storage tank 2 rotates in a direction of the arrow A about a central shaft M including the distributor 21. Since the above-described pipes rotate with the storage tank 2, in order to take in or discharge the beer and the gases flowing inside the pipes from or to outside the filler, an interposing means for receiving the flowing objects from the rotating pipes and supplying them to fixed vent pipes (or, in reverse, supplying the beer and gas supplied from outside through fixed supply pipes to the rotating pipes) is required. The distributor 21 is provided as the interposing means.

The distributor 21 is provided in the central part of the annular storage tank 2. A supply pipe 23 for supplying the beer is connected to the distributor 21 from below, and a gas supply pipe 24 for supplying carbon dioxide or nitrogen gas is connected to the upper part of the distributor 21. The beer supplied to the distributor 21 is supplied to the storage tank 2 through twelve pipes 25. The gas supplied through the gas supply pipe 24, such as carbon dioxide or nitrogen gas, is communicated into the storage tank 2 from its upper wall through two gas supply pipes 26. Four vacuum pipes 27 penetrating the inner wall surface of the storage tank 2 are used for discharging gas from inside the container (bottle) to be filled with the beer.

Two vent holes 28 for discharging gas from an upper space inside the storage tank 2 are provided to the upper wall of the storage tank 2. The vent holes 28 are connected to a vent pipe 29 via the distributor 21. The vent pipe 29 is connected to a later-described oxygen concentration measuring apparatus.

Further, a dissolved oxygen analyzer 51 is attached inside the supply pipe 23 for supplying the beer so as to measure the amount of oxygen dissolved in the supplied beer.

Figure 3:
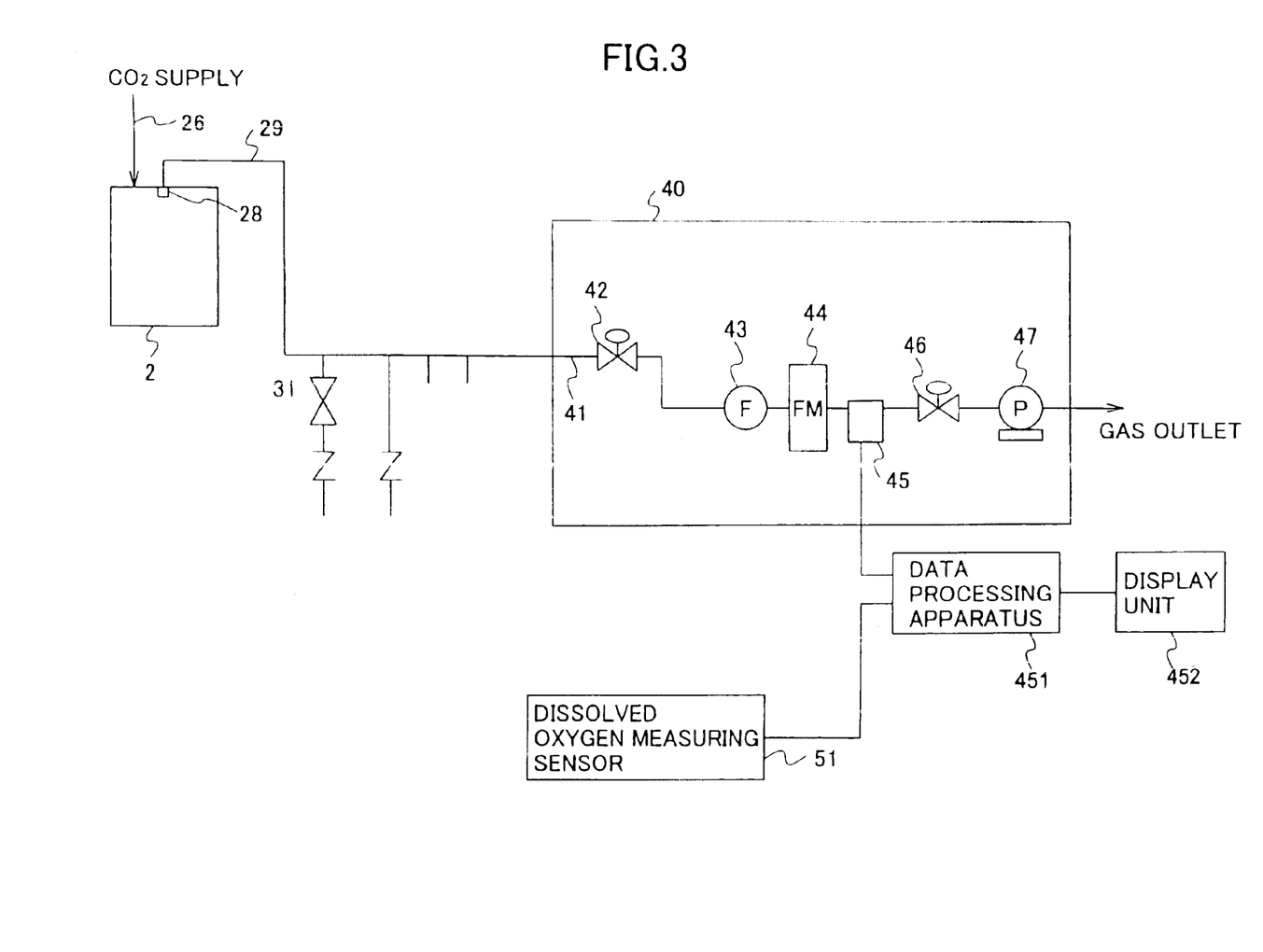
FIG. 3 is a block diagram of a dissolved oxygen amount monitoring system according to the present invention.

FIG. 3 is a schematic diagram for illustrating a dissolved oxygen monitoring system according to the present invention. The vent pipe 29 connected to the vent holes 28 provided to the storage tank 2 of the filler 1 described in FIG. 2 is connected to an oxygen measuring apparatus 40 in order to measure the concentration of oxygen included in the gas in the space part inside the storage tank. Carbon dioxide, which is a replacement gas, is supplied to the storage tank 2 through the pipes 26 so that the upper space is filled with the carbon dioxide.

The oxygen measuring apparatus 40 includes a gas channel 41 connected to the vent pipe 29 extending from the storage tank 2, and has a flow adjustment valve 42, a filter 43, a flowmeter 44, an oxygen measuring device 45, a flow adjustment valve 46, and a pump 47 sequentially along the gas channel 41.

By connecting the thus configured oxygen measuring apparatus 40 to the vent pipe 29 extending from the storage tank 2, the gas in the upper space of the storage tank 2 is continuously introduced into the oxygen measuring apparatus 40, so that the concentration of oxygen included in the gas can be measured. The measurement result obtained by the oxygen measuring device 45 can be constantly monitored by the display unit (not shown in the drawing) of the oxygen measuring device 45. In this embodiment, however, the measurement result is transmitted to a data processing apparatus 451 to be processed so that necessary information can be obtained. That is, the allowable level of the concentration of oxygen gas included in the carbon dioxide is set beforehand as a reference value and compared with a measurement value measured by the oxygen measuring device 45. It is determined that the amount of oxygen included in the space part inside the storage tank 2 exceeds the allowable level when the measurement value exceeds the reference value, and the determination result is displayed on a display unit 452. Instead of a visual warning method shown in this embodiment, an auditory warning such as sound may be given based on a warning signal supplied from the data processing apparatus 451, or production lines may be stopped.

The data processing apparatus 451 may be capable of calculating the concentration of the carbon dioxide inside the storage tank 2, or a rate of replacement by the carbon dioxide in the space part inside the storage tank, from the concentration of the oxygen gas included in the carbon dioxide. In this case, the rate of replacement by the carbon dioxide can be an index for monitoring the amount of oxygen included in the space part inside the storage tank.

Here, the concentration of carbon dioxide is calculated from the concentration of oxygen by the following equations:

Oxygen concentration÷0.209=amount of air (1)

100−amount of air=carbon dioxide (2)

A dissolved oxygen measuring sensor 51 measures the concentration of oxygen dissolved in the beer flowing through the supply pipe 23. The obtained measurement value is transmitted to the data processing apparatus 451 to be compared with a given level. When the value exceeds the given level, an alarm signal is output to the display unit 452.

In this embodiment, a thermoparamagnetic oxygen sensor is employed as the oxygen measuring device 45 used in the oxygen measuring apparatus 40. Here, a description will be given of the principles of measurement of the thermoparamagnetic oxygen sensor.

The thermoparamagnetic oxygen sensor operates on the principle of magnetic wind. Unlike most other gases, oxygen is greatly affected by a magnetic field so as to be drawn to the central part of the magnetic field.

The influence of the magnetic field is inversely proportional to temperature. Therefore, when a sample gas including oxygen is heated, the influence of the magnetic field decreases. Accordingly, by heating the central part of the magnetic field, a drawn sample gas is driven out of the central part of the magnetic field by sample gas that is drawn subsequently. Repetition of this generates flow (magnetic wind), which depends on the concentration of oxygen.

Figure 4:
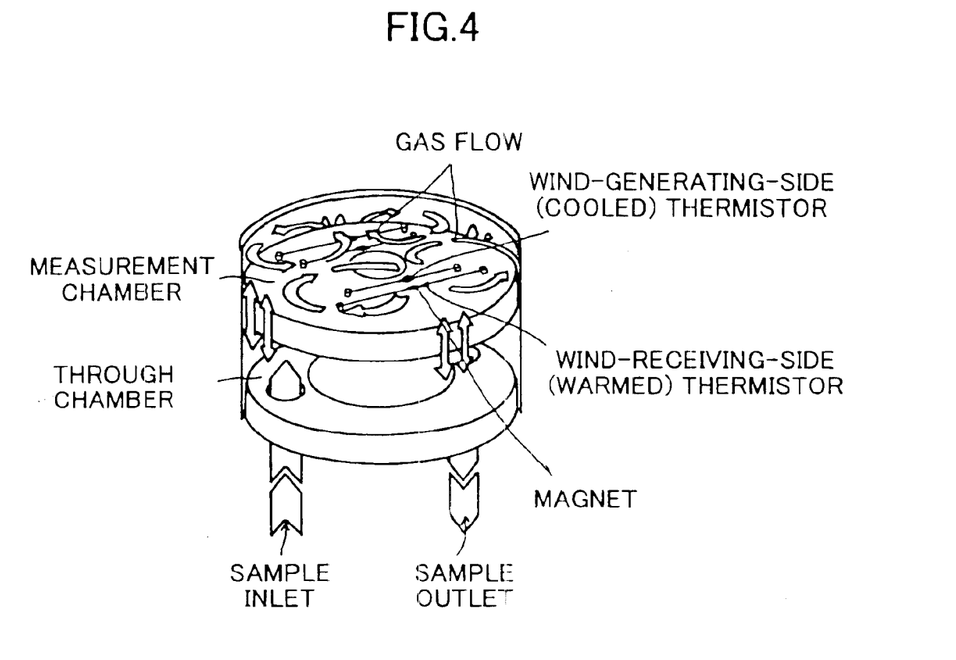
FIG. 4 is a diagram illustrative of a thermoparamagnetic oxygen measuring device.

FIG. 4 is a diagram for illustrating gas flow inside the measurement chamber of the thermoparamagnetic oxygen sensor. A pair of wind-generating-side and wind-receiving-side thermistors are provided on a magnet inside the measurement chamber. An electric current is controlled so that each thermistor is heated to a constant temperature. The influence of a magnetic field produced by the magnet on oxygen drawn to the magnetic field is decreased by the heated thermistors so that flow is generated. This flow robs heat of the inner (wind-generating-side) thermistor so that the inner thermistor is cooled. The outer (wind-receiving-side) thermistor is warmed by the wind that has robbed the heat. The thermistors form a bridge circuit, and the balance is varied by the flow. By measuring a variation in the balance, the concentration of oxygen can be measured. Therefore, by employing the above-described thermoparamagnetic oxygen sensor in the oxygen measuring apparatus 40, the concentration of oxygen in the gas can be measured while the gas is continuously introduced.

Figure 5:
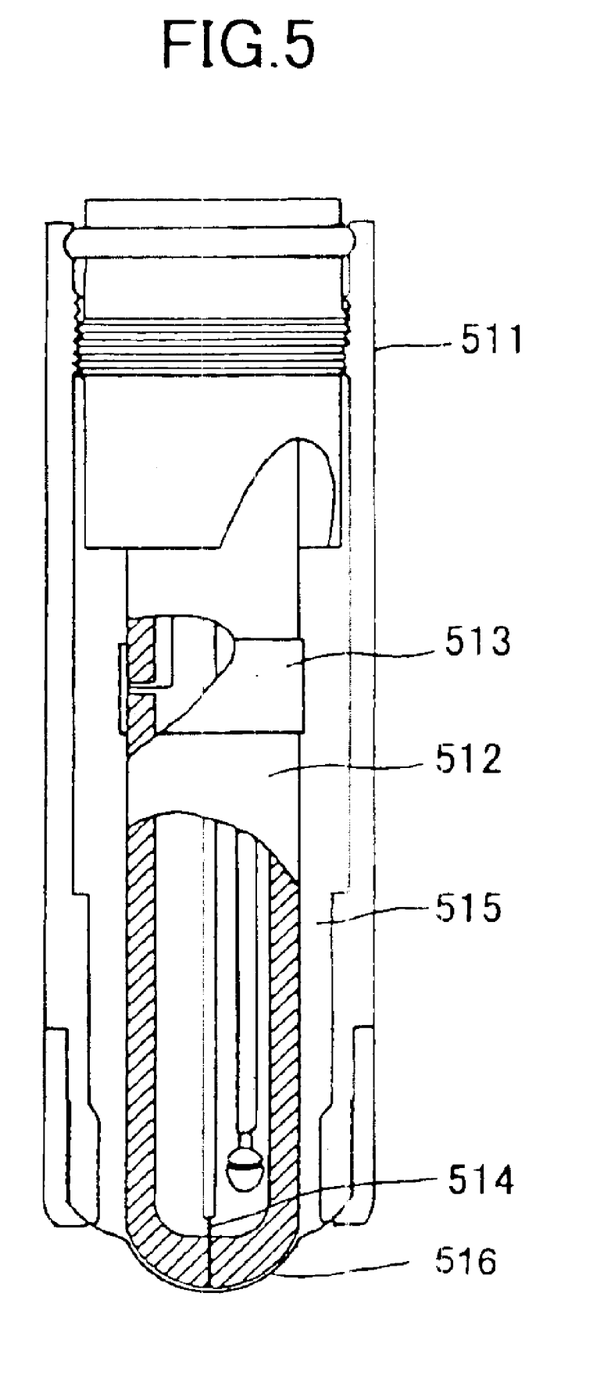
FIG. 5 is a diagram illustrative of a dissolved oxygen analyzer.

FIG. 5 shows an example of the dissolved oxygen measunug sensor 51 employed in this embodiment. The dissolved oxygen measuring sensor 51 used herein employs a polarographic amperometric method and has electrodes formed of a cathode and an anode coupled by an electrolyte. As represented graphically, the dissolved oxygen sensor 51 is composed of a main body 511, a glass tube 512, an anode 513, a cathode 514, an electrolyte 515, and a diaphragm 516 at the tip. The anode 513 and the cathode 514 are coupled by the electrolyte 515. Liquid to be examined and the electrodes are separated by the diaphragm 516 that is a gas-permeable film. Oxygen molecules passing through the permeable film 516 are reduced by a polarographic potential applied to the cathode 514. At this point, an electric current proportional to the partial pressure of oxygen is generated. By measuring the electric current, the amount of oxygen dissolved in the examined liquid can be measured.

Next, a description will be given, based on FIGS. 2 and 3, of an oxygen concentration measuring and monitoring system used for the filler 1 of the present invention.

Beer to be filled into the bottles is supplied from the distributor 21 to the storage tank 2 via the beer supply pipes 25.

As previously described, the filler is of a rotary type. As shown in FIGS. 1 and 2, the entire filler 1 including the storage tank 2 rotates about the central shaft M with the containers 10 circulating accordingly, while the beverage inside the storage tank 2 is filled thereinto through the filling valves 3. During this period, carbon dioxide is supplied to the space part inside the storage tank 2 through the gas supply pipes 26 so as to replace air (oxygen) inside the space part.

As for the filling procedure of the beer, first, air inside the containers is discharged through the vacuum pipes 27, and then the carbon dioxide is filled into the containers so as to replace the air therein. After being filled with the carbon dioxide, the containers are filled with the beer. The carbon dioxide that is discharged at this point is sent out into the storage tank 2.

In a series of the above-described beer filling operations, the gas in the space part inside the storage tank 2 is sampled so that its oxygen concentration is measured, while the concentration of oxygen dissolved in the beer supplied to the storage tank 2 is measured. Based on both of the measured values, monitoring is performed so as to prevent oxygen from deteriorating the flavor of the beer.

Concerning monitoring of the concentration of oxygen in the gas in the space part of the storage tank 2 in oxygen concentration monitoring by the thus configured oxygen concentration measuring and monitoring system, the gas in the upper space of the storage tank 2 is supplied from the vent holes 28 to the oxygen measuring apparatus 40 shown in FIG. 3 via the vent pipe 29. The gas introduced into the oxygen measuring apparatus 40 is adjusted to a given amount of flow by the flow adjustment valve 42 to be delivered to the oxygen measuring device 45 via the filter 43 and the flowmeter 44. The oxygen measuring device 45, which is a thermoparamagnetic oxygen measuring device in this embodiment, measures the concentration of oxygen in the gas supplied continuously. The measurement value of the oxygen measuring device 45 is monitored, and the concentration of oxygen in the gas is constantly monitored by the display unit 452 showing the result of comparison with the reference value in the data processing apparatus 451.

Further, in measuring the concentration of oxygen in the beer, the amount of oxygen dissolved in the beer is constantly monitored by having the concentration of dissolved oxygen measured constantly by the dissolved oxygen measuring sensor 51 and compared with a reference value in the data processing part 451.

Thus, in the oxygen concentration measuring and monitoring system of this embodiment, the amount of oxygen included in the vapor phase of the space part contacting the beer inside the storage tank can be measured and monitored continuously, and the concentration of oxygen in the beer immediately before filling can be monitored in real time.

In the above-described embodiment, in monitoring the concentration of oxygen in the beer, the amount of dissolved oxygen is measured from the beer inside the supply pipe 23 for supplying the beer to the storage tank 2. If the concentration of oxygen in the beer shows a value greater than the reference level by this, it can be understood that the cause of oxygen dissolution lies in a process prior to the filling process. In measuring the concentration of oxygen in the beer inside the storage tank, the beer may be sampled from inside the storage tank.

As described above, according to the present invention, the effect of oxygen before filling containers with beer in the production process thereof can be measured and monitored, so that the beer can be prevented in advance from being produced with its flavor being deteriorated by the effect of oxygen. Thereby, the best products having excellent flavor durability can always be produced.

In the above-described embodiment, the description is given of the case where a thermoparamagnetic oxygen sensor is employed as the oxygen sensor of the oxygen measuring apparatus, while an oxygen sensor of another type, such as a galvanic cell type oxygen sensor, may be employed. However, if the main component of gas to be measured is carbon dioxide as the gas of the above-described embodiment, the thermoparamagnetic oxygen sensor, which is less subject to deterioration by carbon dioxide, is superior.

Another type of dissolved oxygen analyzer than that shown in FIG. 5 is also employable.

In the above-described embodiment, the description is given of an apparatus for monitoring the amount of oxygen dissolved in the beer inside the storage tank of the beer filler, while, needless to say, the present invention is applicable to fillers of beverages other than beer, such as tea beverages including tea and green tea and alcoholic beverages including sparkling liquor.

Further, carbon dioxide is described as a replacement gas to replace the gas inside the storage tank, while another gas such as nitrogen gas is applicable as the replacement gas.

EFFECTS OF THE INVENTION

As is apparent from the above detailed description, according to the present invention, the amount of oxygen, which affects the flavor of a beverage, is constantly measured and monitored immediately before the beverage is filled into beverage containers, and a warning is issued when it is determined that the amount of oxygen reaches a level where its effect is not negligible. Therefore, the beverage is prevented in advance from being filled with oxygen included therein, so that beverage products having excellent flavor durability can be provided.

Further, in a rotary beverage filler, gas in a space part inside a beverage storage tank can be sampled continuously from the rotating beverage tank through a distributor provided in the rotation center part of the beverage storage tank so that the concentration of oxygen in the gas can be continuously monitored.

What is claimed is:

1. A method of monitoring a concentration of oxygen in a beverage production process, the method comprising the steps of:

(a) continuously sampling gas in a space part inside a beverage storage tank storing a beverage to be filled, the beverage storage tank being provided to a beverage filler;

(b) measuring a concentration of oxygen in the sampled gas;

(c) comparing the measured concentration of oxygen in the sampled gas and a preset first reference concentration;

(d) issuing an alarm signal when the measured concentration of oxygen in the sampled gas exceeds the first reference value;

(e) continuously measuring a concentration of oxygen included in the beverage flowing through a beverage supply channel supplying the beverage to the beverage storage tank storing the beverage to be filled, the beverage storage tank being provided to the beverage filler, (f) comparing the measured concentration of oxygen in the beverage with a preset second reference value; and (g) issuing an alarm signal when the measured concentration of oxygen in the beverage exceeds the second reference value.

2. An apparatus for monitoring a concentration of oxygen in a beverage production process, the apparatus comprising:

a sampling part continuously sampling gas in a space part inside a beverage storage tank storing a beverage to be filled, the beverage storage tank being provided to a beverage filler;

a first measuring part measuring a concentration of oxygen in the sampled gas;

a first comparison part comparing the measured concentration of oxygen in the sampled gas and a preset first reference concentration;

a first determination part issuing an alarm signal when the measured concentration of oxygen in the sampled gas exceeds the first reference value;

a second measuring part continuously measuring a concentration of oxygen included in the beverage flowing through a beverage supply channel supplying the beverage to the beverage storage tank storing the beverage to be filled, the beverage storage tank being provided to the beverage filler;

a second comparison part comparing the measured concentration of oxygen in the beverage with a preset second reference value; and a second determination part issuing an alarm signal when the measured concentration of oxygen in the beverage exceeds the second reference value.

3. The apparatus as claimed in claim 2, further comprising:

a flow channel for the sampled gas to flow through to an outside of the beverage storage tank; and a distributor for receiving the sampled gas from the flow channel and delivering the sampled gas to said first measuring part outside the beverage filler, wherein said first measuring part constantly measures the concentration of oxygen in the sampled gas.

4. The apparatus as claimed in claim 3, wherein said distributor is provided to a rotary center shaft of the beverage storage tank provided to the beverage filler, the beverage filler being of a rotary type.

* * * * *